(12) United States Patent
Ruff et al.

(10) Patent No.: US 10,913,031 B2
(45) Date of Patent: Feb. 9, 2021

(54) MONITORING A REVERSE-OSMOSIS DEVICE USED WITH DIALYSIS DEVICES

(71) Applicant: Fresenius Medical Care Deutschland GmbH, Bad Homburg (DE)

(72) Inventors: Christian Ruff, Oberursel (DE); Thomas Pohl, Friedrichsdorf (DE); Michael Wild, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 139 days.

(21) Appl. No.: 16/169,688

(22) Filed: Oct. 24, 2018

(65) Prior Publication Data
US 2019/0143273 A1 May 16, 2019

(30) Foreign Application Priority Data
Nov. 13, 2017 (DE) .......................... 10 2017 126 592

(51) Int. Cl.
*B01D 61/02* (2006.01)
*A61M 1/16* (2006.01)
(Continued)

(52) U.S. Cl.
CPC ......... *B01D 61/025* (2013.01); *A61M 1/1601* (2014.02); *A61M 1/1656* (2013.01);
(Continued)

(58) Field of Classification Search
CPC .. C02F 1/44; C02F 2209/001; C02F 2209/05; C02F 2209/005; C02F 1/441;
(Continued)

(56) References Cited

U.S. PATENT DOCUMENTS 6,106,723 A * 8/2000 Grandics ................ B01D 61/00
210/198.2
6,120,689 A * 9/2000 Tonelli ................ B01D 61/022
210/180
(Continued)

FOREIGN PATENT DOCUMENTS

| CN | 106110889 A | 11/2016 |
|---|---|---|
| DE | 10 2010 031 530 A1 | 1/2012 |

(Continued)

OTHER PUBLICATIONS

European Patent Office, International Search Report and the Written Opinion in International Application No. PCT/EP2018/080875 (dated Mar. 1 2019).

(Continued)

*Primary Examiner* — Ana M Fortuna
(74) *Attorney, Agent, or Firm* — Leydig, Voit & Mayer, Ltd.

(57) ABSTRACT

The present invention concerns an electronic safety system for an RO device which is configured to be used with at least one dialysis device (e.g., a hemodialysis or a peritoneal dialysis device). The system comprises the RO device, which is configured for the production of ultrapure water and which includes a sensor unit for collecting sensor data and whereby the RO device comprises an electronic data interface in order to send the sensor data collected by the sensor unit; and it also comprises an analysis unit which is configured to analyze a water sample with regards to safety requirements and for example with regard to contamination and to generate result data whereby the analysis unit also includes an analysis interface in order to send the generated result data in electronic form; and a network for the data exchange between the medical entities, for example between the RO device and the analysis unit.

12 Claims, 4 Drawing Sheets

(51) Int. Cl.
*G16H 40/60* (2018.01)
*B01D 61/58* (2006.01)
*B01D 61/12* (2006.01)
*G16H 20/40* (2018.01)
*G16H 40/20* (2018.01)
*G16H 40/63* (2018.01)
*B01D 61/24* (2006.01)

(52) U.S. Cl.
CPC .......... *A61M 1/1694* (2013.01); *B01D 61/12* (2013.01); *B01D 61/58* (2013.01); *G16H 20/40* (2018.01); *G16H 40/20* (2018.01); *G16H 40/60* (2018.01); *G16H 40/63* (2018.01); *A61M 1/168* (2013.01); *B01D 61/243* (2013.01)

(58) Field of Classification Search
CPC .. B01D 2311/04; B01D 61/025; B01D 61/12; B01D 61/22; B01D 1/0082; B01D 37/04
See application file for complete search history.

(56) References Cited

U.S. PATENT DOCUMENTS

| | | | |
|---|---|---|---|
| 7,320,756 B2 * | 1/2008 | Mukhopadhyay | B01D 61/022 210/639 |
| 8,114,259 B2 * | 2/2012 | Zuback | B01D 61/425 204/518 |
| 10,646,634 B2 | 5/2020 | Yu et al. | |
| 2002/0077777 A1 | 6/2002 | Wolfe et al. | |
| 2004/0138840 A1 | 7/2004 | Wolfe | |
| 2010/0332149 A1 * | 12/2010 | Scholpp | C02F 1/008 702/25 |
| 2011/0284480 A1 * | 11/2011 | Karabelas | B01D 35/143 210/767 |
| 2014/0044485 A1 * | 2/2014 | Wallace | B01D 61/025 405/36 |
| 2014/0110304 A1 * | 4/2014 | Wu | B65D 25/54 206/776 |
| 2014/0276375 A1 * | 9/2014 | Minkus | A61L 9/00 604/28 |
| 2014/0291253 A1 * | 10/2014 | Coulter | C02F 1/70 210/746 |
| 2014/0373926 A1 * | 12/2014 | Jha | G01M 99/005 137/2 |
| 2018/0273412 A1 * | 9/2018 | Hall | C02F 1/325 |

FOREIGN PATENT DOCUMENTS

| | | |
|---|---|---|
| DE | 10 2012 109 861 A1 | 4/2014 |
| DE | 11 2013 005 089 T5 | 7/2015 |
| FR | 2911687 A1 | 7/2008 |
| WO | WO 2010/024963 A1 | 3/2010 |
| WO | WO 2012/041970 A1 | 4/2012 |
| WO | WO 2018/094438 A1 | 5/2018 |

OTHER PUBLICATIONS

ISO 13959:2015 "Water for Hemodialysis and Related Therapies," European Committee for Standardization (Dec. 2015).
German Patent Application No. 10 2017 126 592.9, Office Action (dated Jul. 24, 2018).

* cited by examiner

MONITORING A REVERSE-OSMOSIS DEVICE USED WITH DIALYSIS DEVICES

CROSS-REFERENCE TO RELATED APPLICATIONS

Priority is claimed to German Patent Application No. DE 102017126592.9, filed on Nov. 13, 2017, the entire disclosure of which is hereby incorporated by reference herein.

FIELD

The present invention is in the field of water technology for the medical area and may be utilized with respect to providing a safety check for reverse-osmosis devices that are used for medical devices (e.g., dialysis devices) in order to provide the water needed in adequate quality and free from (bacterial) contamination. Exemplary embodiments of the invention include a system, an analysis device, a reverse-osmosis device, a server, a method and a computer program product relating to providing a safety check on water that is fed into medical devices.

BACKGROUND

Dialysis devices operate with ultrapure water. To be able to provide ultrapure water, reverse-osmosis (RO) devices are being used.

In a reverse-osmosis process, a natural osmosis process is reversed via pressure. An illustrative RO process can be described as follows: two containers are filled with liquid (e.g., water) of disparate substance content (e.g., salinity), which are separated from each other by a semipermeable membrane; after the application of an osmotic pressure in the container where the concentration is to be raised, the molecules of the solvent can migrate against their "natural" osmotic direction of propagation; for this process, the applied pressure must be higher than the pressure that arises from the osmotic desire to equalize concentration; the method pushes the molecules into the compartment in which the dissolved substances are less concentrated. With this method, the concentration of unwanted substances on the side of ultrapure water can be reduced.

The water produced via an RO device is applicable in the medical area and for example, for the operating of dialysis machines (e.g. the hemodialysis system 5008 by Fresenius Medical Care and other extracorporeal blood treatment devices).

To adhere to the strict safety requirements of medical devices, water is to be provided with the required quality. For this purpose, the ultrapure water produced in an RO device is checked for its adherence to the chemical and microbiological safety requirements in defined time intervals. This takes place in external laboratories. The conditions for the check are defined in the standard ISO 23500 "Guidance for the preparation and quality management of fluids for haemodialysis and related therapies."

Generally, a water sample of ultrapure water is taken from an RO device or the connected ring line and is sent to a laboratory. The laboratory usually requires several days for providing a lab report or result which is forwarded to the operator of the RO device via post or telephone call.

This conventional procedure has the substantial disadvantage that it can take several days or up to a week until the lab result is available on the local device. If the result indicates a contamination with bacterial germs or another safety fault, the connected dialysis devices can be turned off by the RO device only after the information has been forwarded locally to the RO device. Prior to being turned off, a safety risk exists because the devices continue to be operated with bad water quality. In such a case, this conventional procedure poses a safety issue.

SUMMARY

In an exemplary embodiment, the invention provides a safety system for monitoring a reverse-osmosis (RO) device configured for use with one or more dialysis devices. The system comprises: the RO device, wherein the RO device is configured to produce ultrapure water and comprises a sensor unit for collecting sensor data, and wherein the RO device further comprises an interface for transmitting the sensor data collected by the sensor unit; and an analysis unit, configured to analyze a water sample of the RO device and to generate result data regarding contamination, wherein the analysis unit comprises an interface for transmitting the result data. The RO device and the analysis unit are configured to communicate via a network.

In another exemplary embodiment, the invention provides a method for safety-related monitoring of a reverse-osmosis (RO) device configured for use with one or more dialysis devices. The method comprises: collecting, by the RO device, sensor data during the operation of the RO device, wherein the RO device is configured to produce ultrapure water; transmitting, by the RO device, the collected sensor data to another device; analyzing, by an analysis unit, a water sample from the RO device with regard to safety requirements and generating result data based on the analysis; and transmitting the generated result data to the RO device and/or to the one or more dialysis devices.

In yet another exemplary embodiment, the invention provides a non-transitory memory having processor-executable instructions stored thereon for safety-related monitoring of a reverse-osmosis (RO) device configured for use with one or more dialysis devices. The processor-executable instructions, when executed, facilitate performance of the following: collecting, by the RO device, sensor data during the operation of the RO device, wherein the RO device is configured to produce ultrapure water; transmitting, by the RO device, the collected sensor data to another device; analyzing, by an analysis unit, a water sample from the RO device with regard to safety requirements and generating result data based on the analysis; and transmitting the generated result data to the RO device and/or to the one or more dialysis devices.

BRIEF DESCRIPTION OF THE FIGURES

Exemplary embodiments of the present invention will be described in even greater detail below based on the exemplary figures. The invention is not limited to the exemplary embodiments. All features described and/or illustrated herein can be used alone or combined in different combinations in embodiments of the invention. Features and advantages of various embodiments of the present invention will become apparent by reading the following detailed description with reference to the attached drawings which illustrate the following.

DETAILED DESCRIPTION

Figure 1:
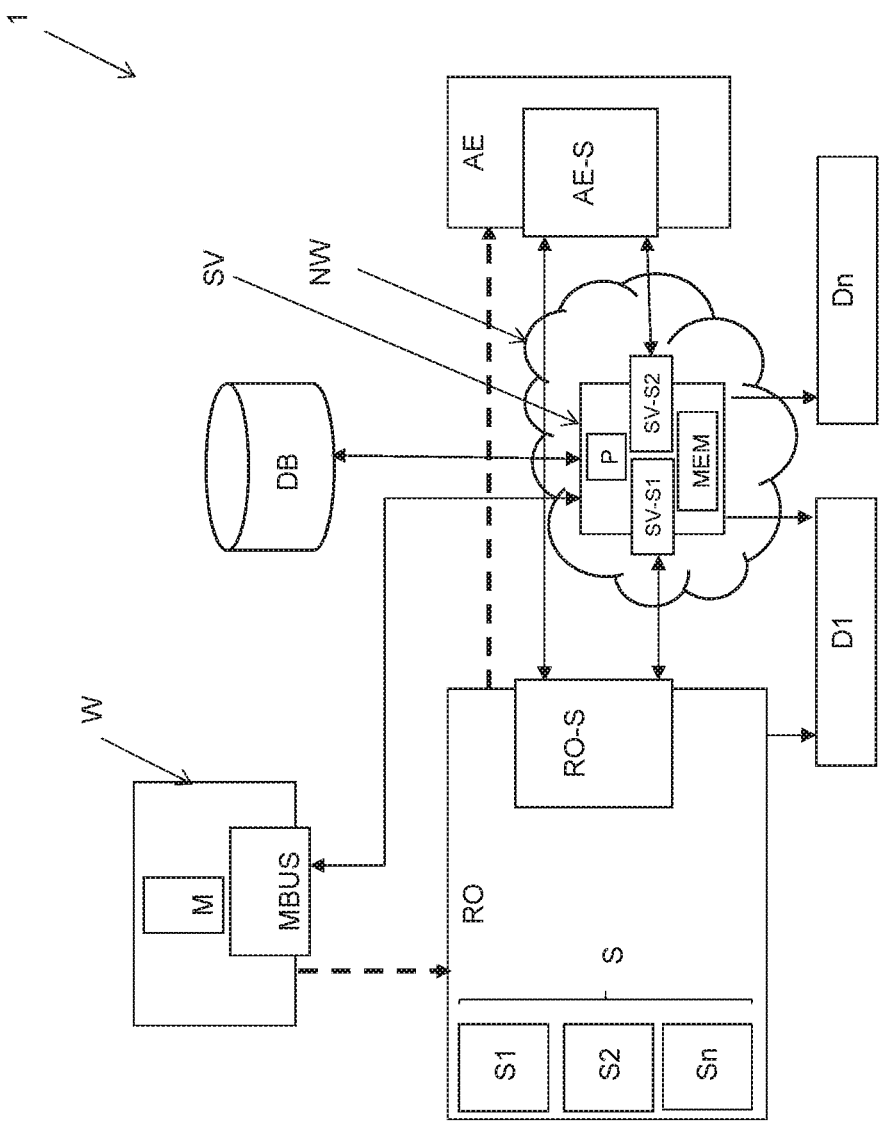
FIG. 1 shows in a schematic representation a safety system with an RO device for the operation of dialysis devices and a server and their data exchange according to an exemplary embodiment of the invention.

Exemplary embodiments of the invention improve the safety of RO devices and medical devices connected thereto. Additionally, exemplary embodiments of the invention improve analytical ability with respect to collected captured data (sensor data, laboratory value, etc.). Additionally, exemplary embodiments of the invention provide the data relevant to safety relatively earlier. Furthermore, exemplary embodiments of the invention improve the provided information with the help of technical messages and allow the provided information to be directly and locally used on a device.

Exemplary embodiments of the invention include an electronic safety system, an analytic unit, an RO device, a server, a method, and a computer program product.

It will be appreciated that features of the invention described herein in connection with a particular exemplary embodiment of the invention (e.g., features relating to an electronic safety system) may also be applicable to other exemplary embodiments of the invention (e.g., an analytic unit, an RO device, a server, a method, and a computer program product).

According to a first aspect, the invention concerns an electronic safety system for an RO device, whereby the safety system can be operated as a central, server-based (e.g., cloud-based) system for securing sufficient ultrapure water quality and whereby the RO device is built for the use and/or operation with a network of medical devices, for example dialysis devices. The safety system comprises:

The RO device that is configured to produce ultrapure water and includes a sensor for determining sensor data, for example of a conductivity before and after the membrane with a retention and whereby the RO device comprises an electronic data interface to exchange analog and/or digital data in order to send the sensor data determined by the sensor unit to an external entity outside of the RO device;

An analysis unit which can be disposed, for example, in a laboratory for examining the water quality and which is configured to analyze a water sample from the RO device regarding the safety requirements for the ultrapure water (e.g. in regards to contaminations) and to generate result data, whereby the analysis unit includes an analysis interface in order to send the generated result data in electronic format to an external entity outside of the analysis unit;

A network for the data exchange between medical components of the safety system, for example between the RO device and the analysis unit.

According to an embodiment, the system comprises a server which is configured to receive the sensor data of the RO device and/or the result data of the analysis unit and that is furthermore configured to transfer the result data to the RO device and/or the medical devices that are connected to the RO device for the purpose of operating. If necessary, the result data can be transferred to other devices which are integrated in the respective entity (hospital/hospital unit) in which the RO device is installed. This embodiment of the invention has the advantage that the server can be implemented in the cloud and thus can provide sufficient technical resources (e.g. CPU power, storage capacity, implementation of applications for the purpose of evaluation or for other purposes). Furthermore, this enables a central processing and an aggregation of data, whereby the generated data can be transferred quickly and in time to the peripheral clients (e.g. medical devices, RO device) via a network connection or the respective control interface.

Another technical advantage is to be seen in the fact that the RO device and/or the dialysis device can directly access the result data. If the result data indicates, for example, a deficiency regarding the water quality, this can be transferred directly to the receivers, and thus the dialysis devices, as early as possible in order to disconnect them from the RO water system or, if possible, exchange it for another connection. Additionally, the evaluation system on the server can access a rule base that is dynamically adaptable during operation in which there are provided rules which define, for example, that in the case of an error a warning message has to be generated and sent to different computer-based or electronic reception accounts (e.g., mobile terminals of a ward physician or computer in the nurses' station) to permit quick actions.

The server with the evaluation application can additionally receive further data from other data sources, for example, from a water supply unit which is configured to supply the RO device with water or from other devices that are connected to the RO device or are supplied by it or operated by it. The water supply unit may include a measuring unit in order to determine the water consumption data and transfer them to the server. The server can provide a first result on the basis of the transferred water consumption data and/or sensor data according to an embodiment of the invention. For this, there can be provided an evaluation unit on the server which evaluates the received data on the basis of a deposited rule data set. The rule data set can be changed dynamically during the operation of the system, too.

A rule can be, for example: "If the sensor data fall below or exceed a predefinable threshold value, the water quality is not sufficient" or "If the sensor data lie within a predefinable interval and the water consumption data lie below a threshold value, the water quality is sufficient." The preliminary result determined in this manner can either be issued on the server via a user interface (e.g., in the first example above as a warning message) and/or can be transferred to the RO device and further devices.

However, this preliminary result is based solely on the measured values and the sensor data. In order to validate the preliminary result, another analysis is provided. For this purpose, a water sample is analyzed in the analysis unit. Afterwards, result data can be provided. These data can be transferred to the server in order to validate or invalidate the preliminary result. Depending on the outcome, the result data are issued again on a user interface of the server and/or are transferred to the RO device or further devices. The latter occurs for example when the quality has been evaluated as deficient in order to take countermeasures and disconnect for example the dialysis devices from the water network. Thereby, the quality of the evaluation can be improved and a statement on the quality can be provided independently of an analysis on the laboratory scale. The RO device can thus be advantageously monitored fundamentally more closely. Furthermore, it is reversely possible to specify the analysis result, which comes from the laboratory analysis, via the sensor data and/or the consumption data or, where applicable, it is possible to locate or indicate a reason. The application for the evaluation and validation—as described precedingly—does not have to be carried out on the server, but can also be swapped out, e.g. directly to the RO device or to the analysis unit.

In another advantageous embodiment of the invention, the system comprises additionally a water supply unit which is configured for the supply of water to the RO device and wherein the water supply unit comprises a measuring unit for measuring water consumption data and wherein the measuring unit comprises a bus interface to forward the determined water consumption data (in particular, for example, to the server). With these data, more comprehensive evaluation processes can be started, and more comprehensive results can be provided. That way, an analysis result can time-wise be assigned to the water consumption data in order to be able to provide a more expansive statement. For consumption data (e.g. water consumption per hour/day/week/treatment), threshold values can be defined. If such a threshold value is exceeded, a message is issued. Up to that point it remains unclear, why it came to an exceedance. If other water quality data is available (e.g. the conductivity of the raw water or feed water and if this value shows a threshold value exceedance as well), a reason can be already located/indicated with this intelligent connection.

In another advantageous embodiment of the invention, the result data are determined in electronic form in a pre-defined, standardized format. That way, all result data can be processed consistently on the server and/or received on the RO device, even if the analysis units are operated by different operators with different methods and/or applications. This enhances the compatibility of the system and the connected systems.

The sensor data collected by the sensor unit comprise parameters on the conductivity of the water, whereby there are determined two different parameters in particular, namely before and after the membrane (feed water conductivity, permeate conductivity), as well as parameters on retention. The retention R can, for example, be determined with the help of the conductivity of the feed water cSP and the conductivity of the permeate cP as follows:

$$R[\%]=(cSp-cP)/cSp*100.$$

In alternative embodiments of the invention, other parameters can be determined in order to enhance the significance of the analysis or of the evaluation on the server (e.g., electric power and water consumption of the water treatment plant, temperature of the water, water hardness, chlorine concentration).

In another exemplary embodiment, the invention provides an RO device for the production of ultrapure water with a sensor unit for collecting sensor data and with an electronic data interface which is configured for use in a safety system such as the aforementioned safety system.

In another exemplary embodiment, the invention provides an analysis unit for the analysis of a water sample with regards to safety requirements, with the analysis unit being configured to generate result data for each analysis result and send those in electronic form via an analysis interface and with the analysis unit being configured for use in a safety system such as the aforementioned safety system.

In another exemplary embodiment, the invention provides a server for the coordinated processing of safety data of an RO device which is operated for at least one medical device (e.g., a dialysis device), with the server being configured for use in a safety system such as the aforementioned safety system. The server is equipped with:

An electronic data interface for the exchange of digital and/or analog data, in order to receive the sensor data collected by the sensor unit;

An analysis interface to receive the result data generated by the analysis unit in electronic form.

In an advantageous embodiment of the invention, the server has a memory for saving the received data and/or interacts with a database and/or comprises a processing unit for the specific processing of the received data. Thereby, historical data can be processed as well.

In another exemplary embodiment, the invention provides a method for the safety-related check of an RO device for use with at least one medical device (e.g., a dialysis device) with the following method steps:

Collecting sensor data during the operation of the RO device which is configured for the production of ultrapure water;

Sending of the collected sensor data to an external communication partner (outside of the RO device) in electronic form;

Analyzing a water sample of the RO device in regards to safety requirements to generate result data;

Sending the generated result data in electronic form and in particular for the operation of the RO device and/or the dialysis device.

In an embodiment of the invention, the sending of the collected sensor data occurs continuously or in a time-controlled manner during the operation of the RO device and/or according to pre-definable events.

In another embodiment of the invention, the sensor data and the result data are delivered to a server for central processing and are saved there and may be delivered for a statistical evaluation across RO devices.

In another embodiment of the invention, the result data are sent directly to the at least one medical device for the operation of said device in order to trigger locally an emergency stoppage or an emergency stop if necessary.

In another exemplary embodiment, the invention provides a computer program product which comprises a computer program. The computer program comprises software code which is configured for the execution of the abovementioned method. The computer program product can be implemented in software or hardware and can comprise additionally to the computer program a user's manual, a data medium and/or a packaging. In particular, the method steps of collecting, sending and generating result data and their sending via software are triggered and/or executed. Analyzing the sample can comprise several individual operations, which may include user input, and the generating of result data may be fully automatic.

The RO device may be an RO device for the production of ultrapure water and may be used with at least one medical device in order to supply said medical device with ultrapure water. The standard ISO 13959:2014 ("Water for hemodialysis and related therapies") defines the demands on dialysis water (ultrapure water) which an operator of a respective device has to fulfill, and can be used by the producer of those devices and which indicates the following requirements to the microbiological and chemical quality of dialysis water:

| | | Threshold values | |
|---|---|---|---|
| | Medium | Total bacterial count KbE/ml | Endotoxin concentration EU/ml |
| ISO 13959: 2014 Water for hemodialysis and related therapies | Dialysis water | <100 (AL* = 50) | <0.25 (AL* = 0.125) |

*AL = Action level. ISO 13959:2014: concentration from which on steps should be carried out in order to interrupt the trend towards higher, inacceptable values. The value usually lies at 50% of the threshold value.

| | Parameters with proven toxicity during the dialysis | Threshold value [mg/l] | Electrolyte | Threshold value [mg/l] | Trace elements | Threshold value [mg/l] |
|---|---|---|---|---|---|---|
| ISO 1359: 2014 | Aluminium | 0.01 | Calcium | 2 | Antimony | 0.006 |
| | Lead | 0.005 | Potassium | 8 | Arsenic | 0.005 |
| | Fluoride | 0.2 | Magnesium | 4 | Barium | 0.1 |
| | Total chlorine | 0.1 | Sodium | 70 | Beryllium | 0.0004 |
| | copper | 0.1 | | | Cadmium | 0.001 |
| | Nitrate as (N) | 2 | | | Chromium | 0.014 |
| | Sulfate | 100 | | | Mercury | 0.0002 |
| | Zinc | 0.1 | | | Selenium | 0.09 |
| | | | | | Silver | 0.005 |
| | | | | | Thallium | 0.002 |

The correct operational capability of the RO device is defined, among other things, based on the retention of sodium chloride (common salt), which—depending on the profile of requirements to the ultrapure water—should lie between 90% and 99.8%.

The analysis unit can be a part of a laboratory system for the examination of water samples. The analysis unit may be an electronic component and provides for digital data processing and for communicating the data to external communication entities. Apart from the analysis unit, the laboratory system may comprise apparatuses and devices on the laboratory scale (e.g., a conductivity meter, an ion chromatograph, a mass spectrograph or an atomic absorption spectrometer for the quantitative determination of single ions, etc.). The laboratory system provides for detecting contamination of the water as well as for carrying out a biological and/or chemical analysis as well as bacteriological examination. Result data—e.g., in the form of an electronic message—are automatically generated from the carried out analysis via the different, exemplarily mentioned devices above and are prepared for sending to external communication partners. The result data may be sent to the RO device and/or to a cloud-based server and/or to the medical devices via a data connection in order to initiate further measures there if necessary.

The network is an electronic network for transferring data. It can be operated with different protocols. Thus, the connection between the RO device and the server can be configured as an MBUS-system (e.g., according to the standard of the series of standards EN13757) and the analysis unit communicates with the server and/or the medical devices via an IP-based protocol (e.g., via messages in an XML structure). For the data exchange, the RO device and/or the analysis unit are configured with interfaces: the RO device with a data interface (e.g. corresponding to an IP-based protocol) and the analysis unit with an analysis interface (e.g. HL7); using these interfaces, the data can be transferred in the form of a table-like data structure (e.g., in the formats of csv, Microsoft Excel or OpenOffice Calc or xml, etc.).

The generated result data can be transferred in the form of status messages (insufficient water quality—sufficient water quality) or in the form of more comprehensive message packages, whereby the message packages comprise further detailed information on the analysis. They can also comprise metadata (e.g., a time stamp, the condition of the sample, the duration of the examination, etc.)

As described above, the system comprises a server, which may be a cloud-based server. On the server, the collected and generated data may be aggregated and saved. For this purpose, access to a connected database can be provided. The server can serve for the concerted processing of data. "Concerted" refers in this context to the fact that the result data have been determined for a network of dialysis devices, namely those dialysis devices that are supplied by the respective RO device. The concerted determination can however also be carried out on a dedicated device, although still centrally for all devices of the network together.

On the server, an evaluation unit in the form of an evaluation application (software) or an evaluation circuit (hardware) can be implemented. The evaluation unit may be an electronic component. The evaluation circuit can, for example, be implemented as an electronic circuit with digital and/or analog circuit components which can implement an evaluation logic. The evaluation logic serves to evaluate which quality levels an analyzed RO device adheres to in order to issue a warning message in case of non-adherence. The warning message can be issued via respective data interfaces to the RO device, to a control unit of the RO device and/or directly to the medical devices (e.g., dialysis devices). For immediate signalling, a traffic light logic can be issued on a user interface (red for too little quality, green for sufficient quality and yellow for warning or exceeding of action levels, e.g., exceeding or going below respective threshold values). The evaluation circuit can access a system of rules for the evaluation, which can be stored on a database or a memory in the form of rules and which defines a policy for prioritization of an amount of result data. The evaluation circuit can be activated automatically if new result data is generated or transferred.

The evaluation may be assigned to a certain RO device. If a central server is used which collects data from all or selected RO devices (e.g. from all devices within a certain geographical region or a dialysis network) and evaluates them, a result across RO devices can be provided via a statistical evaluation. An evaluation that can resolve the messages for the devices according to each RO device identity may also be implemented (e.g. via a respective identification indicator).

In the following, embodiments of the invention are described for a dialysis device as an example for a medical device (e.g. a hemodialysis device). It will be appreciated by a person skilled in the art that the principles described herein can also be used with respect to other medical devices or fluid management machines or blood treatment devices which utilize ultrapure water, as well as peritoneal dialysis devices if they use ultrapure water.

Transferring of sensor data from the RO device and/or of consumption data of the water supply device or another device (e.g., regarding gas consumption, electric power consumption, consumption of temperature resources for heating or cooling, etc.) may be carried out based on a configurable time interval in order to be processed by the evaluation application.

In an embodiment of the invention, it is configurable which devices the result data are to be sent to. For example, it can thus be specified that the data that comprise a highly prioritized warning message (water quality insufficient) are sent to a control unit of the hospital/the operator and to other entities and in a valid case (sufficient quality) are sent only to the server and/or the respective RO device. That has the advantage that devices that run clean are not laded with unnecessary messages. It can however also be desirable and configured that all event types are always available on all devices. That way, the operator (of the clinical institution and/or the RO device) can automatically observe all devices and conditions of the devices at a glance.

In another exemplary embodiment, the invention provides a computer program product which is loaded or loadable into the memory of a computer or of an electronic or medical device with a computer program for executing the method described above if the computer program is executed on the computer or on the electronic or medical device.

In another exemplary embodiment, the invention provides a computer program for executing all method steps of the abovementioned method if the computer program is run on a computer device. The computer program may be stored on a medium that is readable by the computer or the electronic or medical device.

Exemplary embodiments of the invention relate to an electronic messaging service for RO devices which are operated and used for dialysis stations with at least one dialysis device or another medical technical device and which communicate a quality condition of the RO device.

FIG. 1 shows a first embodiment of the invention whereby the system 1 comprises a server SV. The server SV can at least partially be configured to evaluate water quality data. The evaluation of water quality is based on different input parameters which are provided by different devices (RO device RO, analysis unit AE, database DB, etc.).

For this purpose, a safety system 1 is provided which comprises several medical mechanisms, among them medical devices with electronic components each for data processing and communication.

The RO device is configured for the production of ultrapure water which has to be fed to one or more dialysis devices D1, Dn of a dialysis station in order for them to be operated. In order to secure a sufficient quality of the input ultrapure water (adherence to threshold values of contaminations, e.g., of aluminum, chlorine, fluoride, sulphates and/or zinc—the threshold values for a respective maximum concentration are defined as shown above in the standard ISO 13959:2014), the RO device RO is configured with a sensor unit S to collect sensor data (e.g., sensors S1, S2, Sn in FIG. 1). Furthermore, the RO device RO comprises an electronic data interface RO-S to send the sensor data collected by the sensor unit S.

The RO device RO is supplied by a water supply unit W which serves to supply water that can then be cleaned or treated in the RO device RO. The water supply unit W comprises several electronic modules, among others the measuring unit M which serves to determine water consumption data 32. For this purpose, different measuring methods and sensors or signal transmitters can be used. Furthermore, the water supply unit W comprises interfaces for data communication which may be configured as an MBUS interface MBUS. Other medical devices of system 1, e.g., the server SV or the analysis unit AE can communicate via this interface MBUS with the water supply unit W.

The analysis unit AE can be arranged in a laboratory system and is configured to analyze a water sample of the RO device in regards to safety requirements and for example in regards to contamination and to then generate result data for it. The result data are also provided in a digital format, for example in a result format. Hereby it can be a matter of a configurable data structure, for example according to the XML format. Furthermore, the analysis unit AE comprises an analysis interface AE-S in order to send the generated result data in electronic form to external communication partners (e.g., to the RO device RO and/or to the connected dialysis devices D1, Dn).

The units and devices of the safety system 1 are connected via a network NW.

As indicated in FIG. 1, there may be several dialysis devices D1, Dn and/or further units connected to the RO device RO. This is represented in FIG. 1 by the two exemplarily shown devices D1, Dn.

The safety system 1 depicted in FIG. 1 comprises a server SV. It may be centrally accessible via network interfaces via a technical communication network NW and can be configured as a cloud server. The server SV is in a data exchange with the connected devices, for example with the RO device RO, the medical devices D1, Dn, the analysis unit AE and if necessary the database DB. In this first embodiment of the invention, an evaluation application or an evaluation functionality is implemented in a processor P on the server SV which is configured to evaluate the detected data. For example, the result data and the sensor data and if applicable historical data are processed from a database DB according to pre-definable rules in order to indicate a result message about the quality condition of the water provided by the RO device. The result message may be used to operate the RO device and/or the connected dialysis devices D1, Dn. Hereby, the relevant results can be provided directly locally at the point of use. The server SV and the evaluation application implemented in it may be provided as a web-platform and may be browser-based. The server can access a local memory MEM for further calculations (e.g., statistic evaluation) and/or can save the determined or imported data there.

As already described briefly above, the analysis unit AE is configured to generate result data from the lab report or the laboratory results according to a predefined format in order to transfer them to an external communication partner.

In FIG. 1, the dotted arrows (from the water supply unit W to the RO device RO and from the RO device to the analysis unit AE) are meant to indicate that it is not a matter of a data transfer but a transfer of physical mediums, thus in the first case it is water being transferred to the RO device RO and in the second case it is a water sample being transferred to the analysis unit AE. The other arrows indicate the electronic exchange of analog and/or digital data.

Generally, the system can be operated according to multiple embodiments.

As described above, a central server SV is connected to the system 1 in a first embodiment shown in FIG. 1. On the server SV, the evaluation application for evaluating the detected data is implemented. The server SV may be cloud-based and is accessible via IP-based interfaces (e.g. TCP/IP) SV-S1, SV-S2. In this embodiment of the invention, the exchanged data are first sent from the respective sender (e.g., RO device RO, analysis unit AE) to the central server SV which then sends the received data either directly or in pre-processed form to the respective recipient (e.g., RO device RO, analysis unit AE). Furthermore, the data from the water supply unit W and/or the data of the dialysis devices D can communicate via the interfaces SV-S1, SV-S2. Thus, the server SV operates in this embodiment as a proxy or intermediary node in the chain between data source and data sink. This embodiment of the invention has the advantage that all data can be aggregated on the server SV in order to allow for additional evaluation and processing to be carried out. For example, historical datasets can be compared with current datasets in order to be able to provide further statements (e.g. "In 80% of the cases in which the result data indicate an insufficient water quality, the sample has been taken from a group of RO devices that are located in a certain geographic region" or "in 90% of the cases in which the result data indicate an insufficient water quality, the sample has been taken in a certain time phase"). In particular, a statistic evaluation across multiple RO devices can be carried out. Furthermore, the thereby determined reference data can be provided on other RO devices for the purpose of comparison/reference. Furthermore, manually entered data relating to the RO device RO can be considered as well within the scope of the evaluation application. For accessing and saving the data, the memory MEM can be used.

In a second embodiment of the invention there is no central server provided. In this case, the RO device and/or the water supply unit W and/or the dialysis device D interact directly with the analysis unit AE and vice versa. This second embodiment is meant to be represented in FIG. 1 based on the RO device RO communicating directly (without intermediation by the server SV) with the analysis unit AE which is marked by the arrow between the respective interfaces RO-S, AE-S, which runs without intermediation by the server SV. In this case, the evaluation application for evaluating the data and for determining the result message can be provided at least partially on the analysis unit AE. The application can also be partially implemented on other electronic devices. The result data or the result message then comprise a control dataset which is configured for operating the respective device. In case of an error (insufficient ultra-pure water quality), the control dataset can comprise a section that, for example, triggers the issuing of a warning message and/or a deactivation of the RO device RO. Furthermore, the control data set can comprise a notification field which triggers a notification of further entities or devices. This notification is meant to be put into effect for example when the control dataset has been transferred to the external communication partner (e.g. to the RO device RO). For example, warning messages can be triggered automatically directly and locally on the dialysis devices D1, Dn which are connected to the RO device RO. That has the advantage that in cases relevant to safety, the relevant information can be provided directly and locally and thus necessary measures can be initiated directly without having to inform interconnected entities. In an advantageous embodiment, the result data or the result message has to be cleared by a user (e.g., a laboratory consultant) before they are transferred to further devices and entities. This can be carried out via a provided field and a user input determined on said field. The clearing can be tied to different roles of the user (with specific qualifications).

This embodiment is described in greater detail in connection with FIG. 4 further below.

Figure 2:
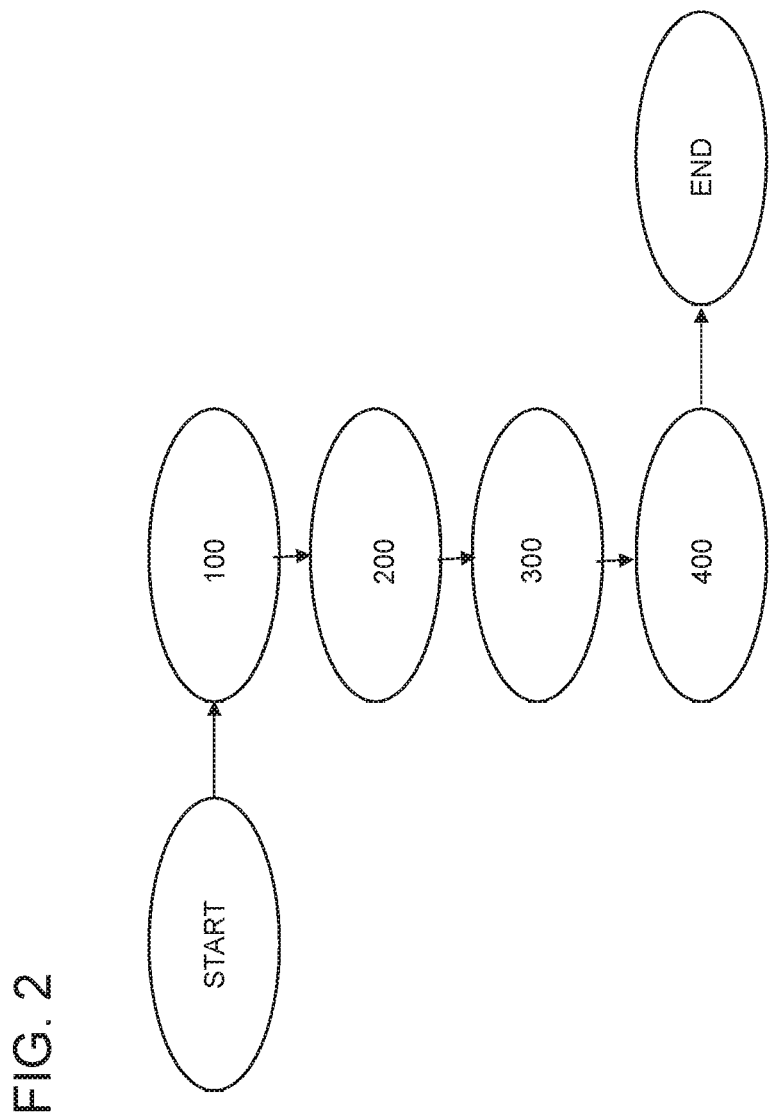
FIG. 2 is a flow chart of a method according to an exemplary embodiment of the invention.

FIG. 2 shows the procedure of the method according to an embodiment of the invention. After the start of the method for the safety-related quality check of an RO device and thus the operation of connected dialysis devices, sensor data are collected in step 100 during the operation of the RO device. This may take place in pre-definable time intervals, after pre-configurable events (e.g. upon connecting another dialysis device and/or after carrying out a certain number of dialyses), or continuously during the operation of the RO device. In step 200, the sensor data collected on the RO device and/or on the water supply unit are sent to an external communication partner (outside of the RO device) in electronic form. The sensor data are transferred to the server SV and/or to the analysis unit AE. The analysis unit AE additionally receives the water sample and analyzes it in order to be able to provide result data. This takes place in step 300. In the following step 400, the generated result data are transferred in electronic form for the operation of the RO device and/or the medical device either directly to the respective devices and/or to the server. They are then processed and transferred from the server SV and can be saved centrally there as well. That way, a first RO device can also access reference data from other RO devices in comparable form. Thereafter, the method can be carried out iteratively or can be ended.

Figure 3:
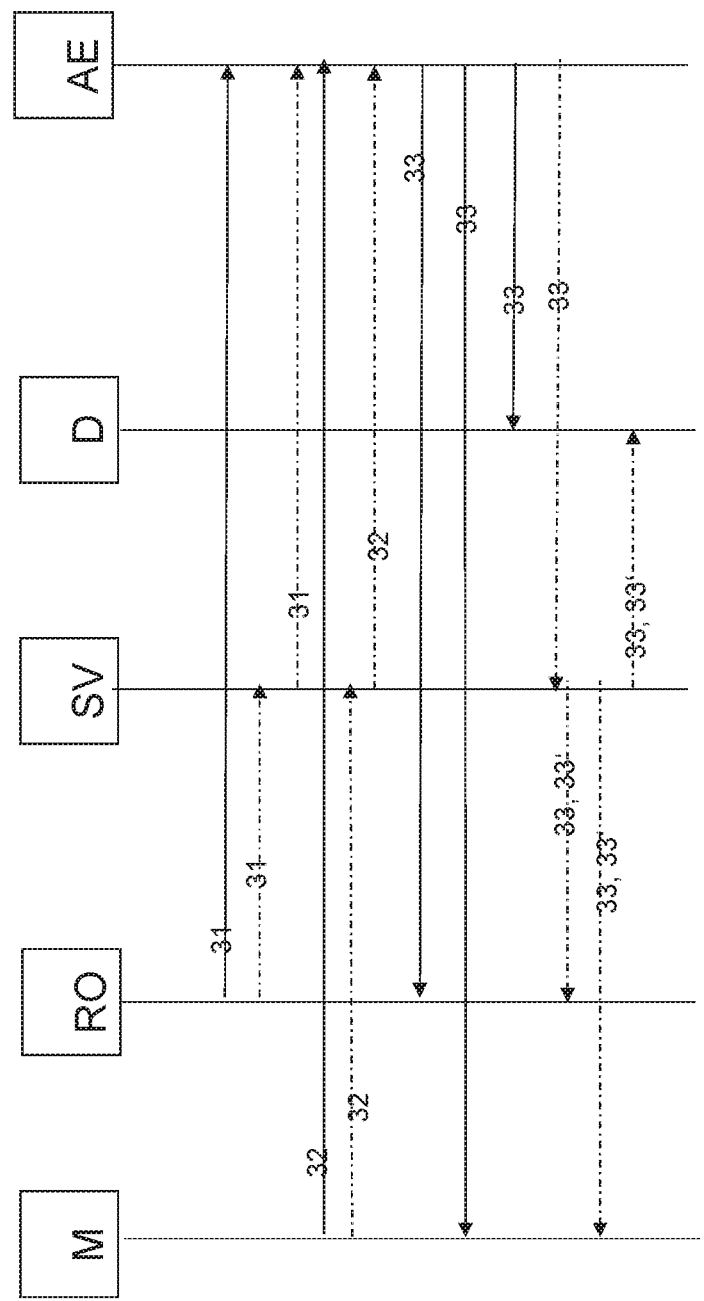
FIG. 3 shows schematically the data exchange between a dialysis device and a server and an RO device according to an exemplary embodiment of the invention.

FIG. 3 shows a sequence diagram with both of the different versions for data exchange between the electronic units of the system 1 as described above:
1. With a central server SV and an evaluation application implemented on it (dot-and-dashed line);
2. Without a server (continuous lines). Here, the RO device and the dialysis device D and the measuring unit M interact directly with the evaluation application that is in this case implemented on the evaluation unit AE.

During the operation of the RO device, sensor data 31 are collected locally and are sent from there directly to the analysis unit AE (continuous arrow). Alternatively, the sensor data are sent first to the server SV and are then sent from there to the analysis unit AE (depicted in FIG. 3 as dot-and-dash). Parallel or simultaneously, water consumption data 32 are collected on the measuring unit M of the water supply unit which are sent to the server SV for the purpose of evaluation in the first version (depicted in FIG. 3 as dot-and-dash). Alternatively or cumulatively, the water consumption data 32 can also be sent to the analysis unit AE (continuous line). In this case, an evaluation application for the evaluation of the data is implemented on the analysis unit AE, so that the respective functionality of the server SV is transferred in this case to the analysis unit AE (represented schematically in FIG. 4). The analysis unit AE generates a result dataset 33 on the basis of the executed laboratory examination or the analysis which is then transferred directly to the devices RO, D, M (continuous lines)—or in the other embodiment via intermediation and/or saving of the server SV which then sends the data in processed or unprocessed form to the recipients RO, D, M (represented in FIG. 3 dot-and-dash). The processing and evaluation on the server SV can comprise further method steps as described above (e.g., a statistic evaluation or a comparison with historical data). The further result of these method steps is indicated in FIG. 3 with the reference sign 33' and can be sent to the respective local entities RO, W, M.

Figure 4:
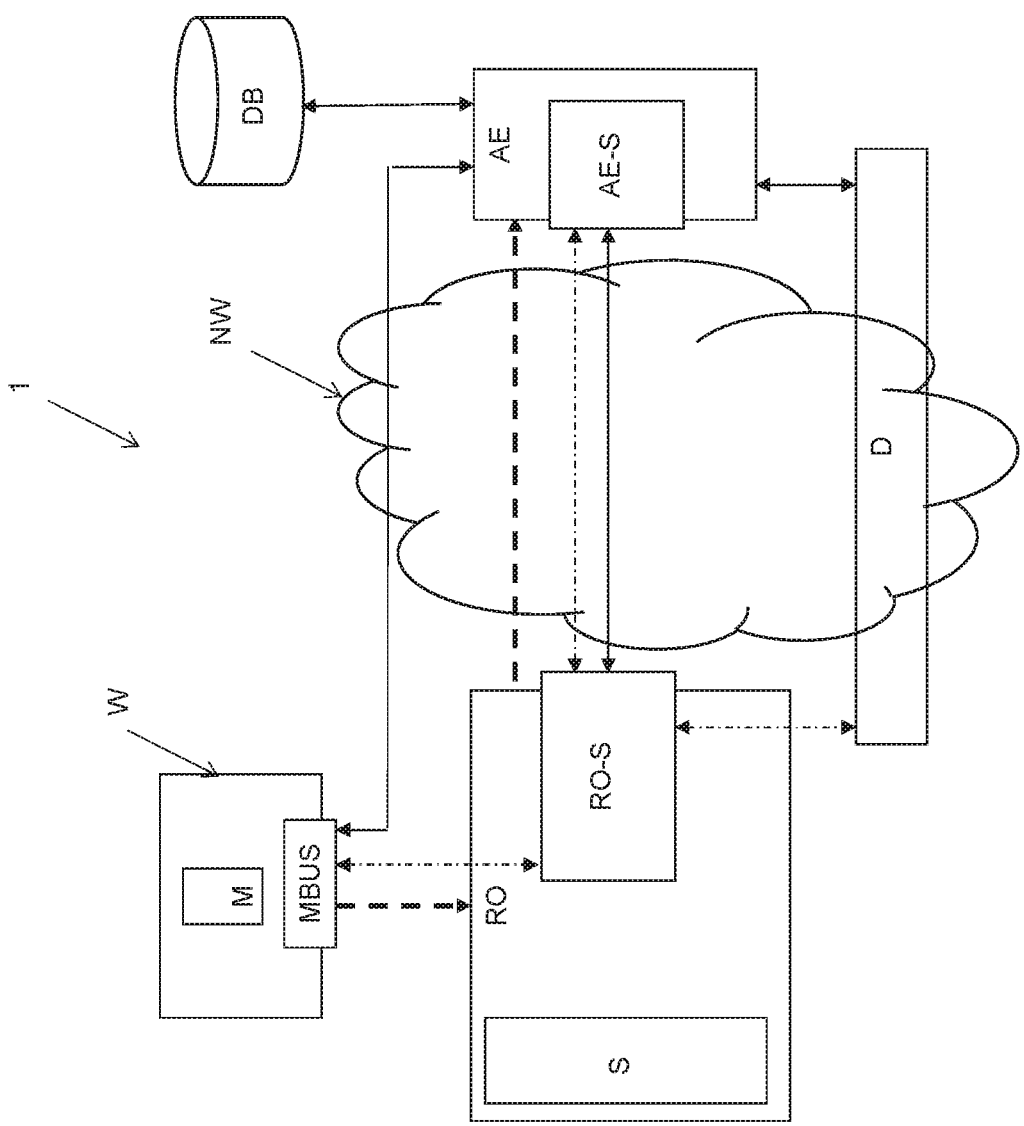
FIG. 4 shows a safety system without a server according to an alternative exemplary embodiment of the invention.

FIG. 4 schematically shows an embodiment whereby the system is operated without a server. The dashed lines (W→RO, RO→AE) do not represent—like in FIG. 1—a data exchange, but the transfer of physical products (water, ultrapure water). Regarding the data exchange, the RO device RO and the analysis unit AE and if applicable the water supply unit W interact with each other directly via a network (e.g., which can be TCP/IP-based). In this embodiment of the invention, the functionality that has been implemented on the server SV in the first embodiment is implemented on the analysis unit AE. The data of the water supply unit W or its measuring unit M, the sensor data of the RO device RO and if applicable the data of the dialysis devices D are sent directly to the analysis unit AE and are processed there. The water supply unit W may also be connected with the RO device RO via a data interface. The data collected on the water supply unit W can then be sent indirectly via the intermediation of the RO device RO to the analysis unit AE. For processing the imported data on the analysis unit AE, reference data can be imported from the database DB and vice versa, the data collected by the analysis unit AE and the processed data can be saved on the database DB. The result of the analysis is either transferred to the RO device (dot-and-dash line) or the data can be sent from the analysis unit AE directly to the water supply unit W for the purpose of operating (this embodiment is indicated in FIG. 4 with the continuous arrow).

It will be appreciated that the foregoing description of the invention and the exemplary embodiments are generally not to be seen as restrictive in regards to certain physical realizations of the invention. All features described and shown in connection with individual embodiments of the invention can be utilized in different combinations according to the invention. It is thus also within the scope of the invention to provide alternatively or cumulatively to the server SV other central units, (e.g., a database). There can also be further medical devices and/or computer-based devices (such as mobile devices) connected to the RO device apart from dialysis devices, on which the result data are issued. It will further be appreciated by a person skilled in the art that the invention can not only be used for dialysis devices, but also for other medical devices which utilize ultrapure water from an RO device for their operation. Thus, for example, the monitoring of the quality of the ultrapure water can also be used for sterilization and cleaning processes for the sterilization of a clinical set of instruments.

Furthermore, the components or modules of a safety system for the monitoring of the quality of the ultrapure water can be distributed across several physical products. It is thus within the scope of the invention that an application for the evaluation of the result data may be completely or partially arranged on an analysis unit or that the application is implemented completely or partially on a server. Additionally, sections of the computer program for executing the method can also be implemented directly on the RO device and/or the medical devices.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A system, comprising:
a reverse-osmosis (RO) device connected to one or more dialysis machines, wherein the RO device is configured to produce ultrapure water and to provide the ultrapure water to the one or more dialysis machines, wherein the RO device comprises one or more sensors configured to collect sensor data, wherein the sensor data comprises a feed water conductivity value, a permeate conductivity value, and/or a retention value;
a server configured to:
receive the sensor data from the RO device;
determine, based on evaluating the sensor data, a preliminary result indicating whether water quality for the RO device is sufficient; and
in response to the preliminary result indicating that water quality is insufficient, issue a warning message; and
a laboratory system, comprising an analysis device configured to:
analyze a water sample corresponding to the RO device; and
generate result data regarding contamination based on analyzing the water sample of the RO device;
wherein the laboratory system is configured to transmit the result data to the RO device via a network;
wherein the RO device is further configured to turn off the one or more dialysis machines in response to receiving result data which indicates contamination.

2. The system according to claim 1, wherein the server is further configured to receive the result data from the laboratory system and send the result data to the RO device and/or the one or more dialysis machines.

3. The system according to claim 2, wherein the server is further configured to validate or invalidate the preliminary result based on the result data.

4. The system according to claim 1, wherein the system further comprises
a water supply device configured to:
supply the RO device with water;
collect water consumption data; and
transmit the water consumption data.

5. The system according to claim 4, wherein determining the preliminary result is further based on evaluating the water consumption data.

6. The system according to claim 1, wherein the server is further configured to aggregate data from a plurality of RO devices.

7. The system according to claim 6, wherein the server is further configured to analyze the aggregated data to evaluate result data corresponding to RO devices from a particular geographic region.

8. The system according to claim 6, wherein the server is further configured to analyze the aggregated data to evaluate result data corresponding to RO devices from a particular time period.

9. The system according to claim 1, wherein the RO device is further configured to determine the retention value R based on the feed water conductivity value cSP and the permeate conductivity value cP according to R [%]=(cSp−cP)/cSp*100.

10. A method comprising:
- collecting, by one or more sensors of a reverse-osmosis (RO) device, sensor data during the operation of the RO device, wherein the sensor data comprises a feed water conductivity value, a permeate conductivity value, and/or a retention value, and wherein the RO device is connected to one or more dialysis machines and is configured to produce ultrapure water and to provide the ultrapure water to the one or more dialysis machines;
- determining, by the RO device or by a server, based on evaluating the sensor data, a preliminary result indicating whether water quality for the RO device is sufficient;
- in response to the preliminary result indicating that water quality is insufficient, issuing, by the RO device or by the server, a warning message;
- receiving, by the RO device, result data corresponding to a laboratory analysis performed on a water sample from the RO device; and
- in response to the received result data indicating contamination, turning off, by the RO device, the one or more dialysis machines.

11. The method according to claim 10, further comprising;
- aggregating, by the server, data from a plurality of RO devices; and
- performing, by the server, statistical evaluations corresponding to the plurality of RO devices.

12. One or more non-transitory memories having processor-executable instructions stored thereon, wherein the processor-executable instructions, when executed, facilitate performance of the following:
- collecting, by one or more sensors of a reverse-osmosis (RO) device, sensor data during the operation of the RO device, wherein the sensor data comprises a feed water conductivity value, a permeate conductivity value, and/or a retention value, and wherein the RO device is connected to one or more dialysis machines and is configured to produce ultrapure water and to provide the ultrapure water to the one or more dialysis machines;
- determining, by the RO device or by a server, based on evaluating the sensor data, a preliminary result indicating whether water quality for the RO device is sufficient;
- in response to the preliminary result indicating that water quality is insufficient, issuing, by the RO device or by the server, a warning message;
- receiving, by the RO device, result data corresponding to a laboratory analysis performed on a water sample from the RO device; and
- in response to the received result data indicating contamination, turning off, by the RO device, machines.

* * * * *